United States Patent
Khaled et al.

(10) Patent No.: US 12,121,504 B1
(45) Date of Patent: Oct. 22, 2024

(54) METHOD FOR PRODUCING 1,3-DIOLEIN FROM BIOMASS

(71) Applicant: KING SAUD UNIVERSITY, Riyadh (SA)

(72) Inventors: Jamal Mohammed Ali Khaled, Riyadh (SA); Naiyf Sultan Helial Alaloi Alharbi, Riyadh (SA); Ramzi Ahmed Abdullah Mothana, Riyadh (SA); Shine Moosa Kadaikunnan, Riyadh (SA); Ahmed Saad Alobaidi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/611,026

(22) Filed: Mar. 20, 2024

(51) Int. Cl.
  *A61K 31/231* (2006.01)
  *A61P 31/10* (2006.01)
  *B01D 15/42* (2006.01)
  *C11B 1/10* (2006.01)
  *C12P 7/6427* (2022.01)

(52) U.S. Cl.
  CPC ............ *A61K 31/231* (2013.01); *A61P 31/10* (2018.01); *B01D 15/426* (2013.01); *C11B 1/10* (2013.01); *C12P 7/6427* (2013.01); *A61K 2236/35* (2013.01)

(58) Field of Classification Search
  CPC ... A61K 31/231; A61K 2236/35; A61P 31/10; C11B 1/10; C12P 7/6427
  See application file for complete search history.

(56) References Cited

PUBLICATIONS

Muto et al (Year: 1970).*
Khojah et al., "Antimicrobial Efficacy of Extracts of Saudi Arabian Desert Terfezia Claveryi Truffles", Saudi Journal of Biological Sciences, vol. 29, Issue 11, Nov. 2022, 103462.
Duan et al., "Sustainable Process for 1,3-DIOLEIN Synthesis Catalyzed by Immobilized Lipase From Penicillium Expansum", ACS Sustainable Chemistry & Engineering, 2015, 3, 11, 2804-2808.
Dawood et al., "Terfezia Boudieri and Terfezia Claveryi Inhibit the LPS/IFN-Γ-Mediated Inflammation in Raw 264.7 Macrophages Through an NRF2-Independent Mechanism", Scientific Reports, 2023; 13: 10106.
Duan et al., "Rational Synthesis of 1,3-DIOLEIN by Enzymatic Esterification", Journal of Biotechnology, May 31, 2012;159(1-2):44-9.

* cited by examiner

*Primary Examiner* — Jeffrey S Lundgren
*Assistant Examiner* — Ibrahim D Bori
(74) *Attorney, Agent, or Firm* — Nath, Goldberg & Meyer; Joshua B. Goldberg

(57) ABSTRACT

A method of using a truffle-derived biomass for producing 1,3-diolein includes obtaining a mycelial biomass from truffles, preparing an extract from the mycelial biomass, and isolating the 1,3-diolein from the extract. In an embodiment, isolating the 1,3-diolein from the extract can include using column chromatography for eluting a portion of a first extract with a mixture including chloroform and methanol into a plurality of fractions, and using column chromatography for eluting at least one of the fractions with methanol to provide 1,3-diolein.

10 Claims, 1 Drawing Sheet

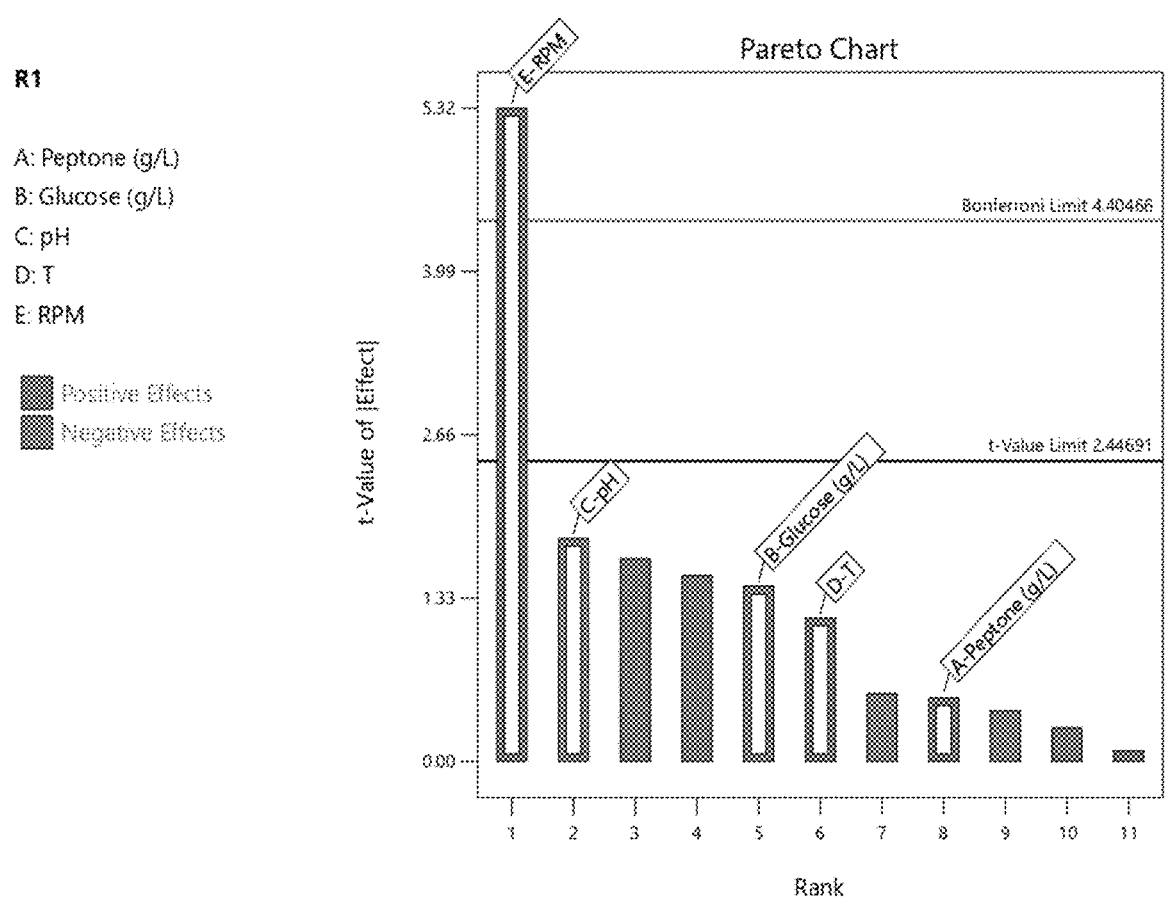

METHOD FOR PRODUCING 1,3-DIOLEIN FROM BIOMASS

BACKGROUND

1. Field

The present disclosure provides a method for producing 1,3-diolein using a mycelial biomass derived from truffles, and, particularly, to a method for producing 1,3-diolein using a mycelial biomass derived from *T. claveryi*.

2. Description of the Related Art

Bioactive compounds usually are extracted and produced from numerous natural biological systems or their derivatives including animals, plants, and microbes. Many studies have confirmed the nutritional importance of desert truffles, but their production is seasonal and depends mainly on special environmental conditions, and research has not succeeded in cultivating them (most of their types) in the laboratory as fruiting bodies.

Production of fatty acids using antimicrobial agents have previously been disclosed, including methods for producing chemical compositions containing conjugated linoleic acids for use in dietary supplements. The nutritional and health benefits of diglycerides have prompted researchers to devise multiple ways to produce the diglycerides. Diacylglycerols, or diglycerides, are significant amphiphilic emulsifiers that are approved by the Food and Drug Administration, USA (FDA) for the application as safe emulsifiers. They are widely used in chemical, food, and pharmaceutical industries.

In 2017, scientific reports indicated that the rate of linoleic acid consumption increased to 6% of the total dietary energy due to its positive role in cardiovascular health and blood cholesterol levels. Until now, an improved method for producing 1,3-diolein from renewable sources that is hygienically safe, has nutritional value, is sustainable, and reliable has not been achieved.

Thus, a method for producing 1,3-diolein from biomass solving the aforementioned problems is desired.

SUMMARY

The present subject matter relates to a method of using a truffle-derived biomass for producing 1,3-diolein. The method can include obtaining a mycelial biomass from truffles, preparing an extract from the mycelial biomass, and isolating the 1,3-diolein from the extract. In an embodiment, isolating the 1,3-diolein from the extract can include using column chromatography for eluting a portion of the extract with a mixture including chloroform and methanol into a plurality of fractions, and using column chromatography for eluting at least one of the fractions with methanol to provide 1,3-diolein.

In an embodiment, a method for producing 1, 3-diolein comprises obtaining a mycelial biomass from *T. claveryi*; preparing an extract from the mycelial biomass; and isolating the 1,3-diolein from the extract. The 1,3-diolein can be used to inhibit fungal growth.

These and other features of the present subject matter will become readily apparent upon further review of the following specification.

BRIEF DESCRIPTION OF DRAWINGS

FIG. 1 is a graph identifying factors that have positive or negative effects on biomass production.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps. It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as a fungal infection.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to a method for producing 1,3-diolein using a truffle-derived biomass. In certain embodiments, the method for producing 1,3-diolein can be a direct fermentation method by fermenting a biomass as described herein. The method can include obtaining a mycelial biomass from truffles, preparing an extract from the mycelial biomass, and isolating the 1,3-diolein from the extract. In an embodiment, the extract can be a chloroform extract. In an embodiment, isolating the 1,3-diolein from the chloroform extract can include using column chromatography for eluting a portion of the chloroform extract into a plurality of fractions with a suitable solvent. In an embodiment, a suitable solvent can include, for example, a mixture including chloroform and methanol, methanol, and ethylacetate:hexane. In an embodiment, a mixture including chloroform and methanol can be used to elute the extract into a plurality of fractions, and methanol can be used for eluting at least one of the plurality fractions to provide 1,3-diolein.

1,3-diolein (also referred to as 1,3-dilinoleate or 1,3-dilinoleoyl glycerol) structurally includes glycerol and two linoleic acids, as shown below:

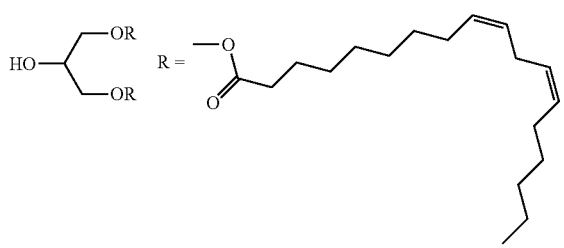

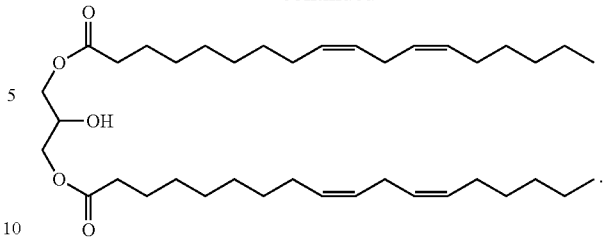

1,3-diolein can demonstrate biological activity against dangerous pathogenic yeasts capable of causing diseases in humans. It has previously been determined that the mechanism by which linoleic acid acts to inhibit hyphal growth in *C. albicans* depends on alternating GTP-binding proteins that are major biochemical elements in the signaling cascade leading to the bio-activation of adenylyl cyclase.

In an embodiment, the truffle-derived biomass can be prepared from desert truffles. The desert truffles can be from the species *T. claveryi*. In an embodiment, the truffle-derived biomass can be a mycelial biomass cultivated using ascospores of *T. claveryi*. The 1,3-diolein obtained therefrom can be used to inhibit fungal growth.

In an embodiment, the truffle-derived biomass can be prepared by mixing a truffle portion with a saline solution to provide a first mixture, centrifuging the first mixture to provide a supernatant including ascospores, adding the supernatant to a broth including peptone and glucose to provide a second mixture, incubating the second mixture to provide a broth including mycelia, and collecting the mycelia.

The present method, as described herein, can provide a renewable natural resource for the production of bioactive compounds. In one embodiment, the ascospores of *T. claveryi* can serve as a production medium for a mycelial biomass, which can then be used to produce 1,3-diolein.

According to an embodiment, the 1,3-diolein produced according to the present methods can be used to inhibit fungal growth. For example, the 1,3-diolein can be used to inhibit growth of *Candida auris* (*C. auris*), particularly fluconazole- and caspofungin-resistant *Candida auris* (*C. auris*) which represents a significant threat to the public. *Candida auris* has a biological ability to survive for weeks on several solid material surfaces such as medical devices and healthcare facilities. This increases the risk of contamination of these surfaces by these dangerous pathogens (Lamont-Friedrich et al., 2022). There has been no prior study evaluating the action of 1,3-diolein on *C. auris*, in particular, antifungal-drug-resistant *C. auris* strains.

As described herein, 1,3-diolein obtained from mycelial biomass exhibits biological activity against fungal agents. According to an embodiment, a method of inhibiting growth of a fungus in a patient can include administering a therapeutically effective amount of 1,3-diolein to the patient. In an embodiment, the fungus is *Candida auris* (*C. auris*). In an embodiment, 1,3-diolein derived from *T. claveryi*. can be used as antifungal agents against fluconazole- and caspofungin-resistant *C. auris*.

In another embodiment, the present subject matter is directed to pharmaceutical compositions comprising a therapeutically effective amount of the 1,3-diolein as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises the 1,3-diolein together with at least one pharmaceutically acceptable auxiliary.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide anti-fungal treatment. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for anti-fungal treatment, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compound can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present subject matter further relates to a method of treating a fungal infection comprising administering to a patient in need thereof a therapeutically effective amount of the compounds herein.

In the above methods, the patient is preferably a mammal, more preferably a human.

The following examples illustrate the present teachings.

EXAMPLES

Example 1

Sample Collection

Samples of truffle, referred to locally as "Khalasi", were collected from a region in northern Saudi Arabia known as Hafar Al-Batin. The samples were washed three times using water. The external surface of the truffle was sterilized three times by ethanol solution (70%) and washed three times using sterilized saline solutions (0.89% of NaCl). A part of the external surface (2-3 mm) was removed using a sterilized sharp knife. The samples were preserved at 20° C. for 24 hours.

The size, color, and shape of the truffles were recorded, and the asci and ascospores were studied using a digital light microscope at 1000×. An internal part of the truffle was placed on a clear microscope glass slide, covered by a cover slip, then tested without using staining steps. It was determined that the truffle samples belong to the species *Terfezia claveryi*.

Example 2

Preparation of Ascopores Suspension

The frozen truffle was left in a sterile hood inside sterile glass bottles at room temperature for an hour, and 1 gm of the internal part of the truffle was vigorously mixed with 10 mL of normal saline solution (0.89% of NaCl) for 10 min. The mixture was centrifuged at 1500×g for 10 minutes. After that, the supernatant was collected. The standard plate method was used to count the total number of the viability of ascopores per mL using potato dextrose agar (50 gm of potato infusion, 5 gm of dextrose and 5 gm of agar per 250 mL of distilled water).

Example 3

Production of Fungal Biomass

A fungal biomass (mycelial biomass) was produced from the ascopores using a broth including peptone and glucose. An optimal broth formulation including optimal glucose and peptone concentrations, optimal incubation temperature, optimal shaking, and optimal pH was determined using Blunkett Burman design and Box-Behnken designs in Design-Expert 13 (Stat-Ease, Inc., United States) (Table 1). Table 1 depicts the results of twelve random experiments designed using Blunkett Burman design to determine the impact of the most important factors affecting biomass production. Then, the response surface methodology method using Box-Behnken design was carried out to optimize the production (Table 2). Table 2 depicts the results of thirteen random experiments designed to optimize biomass production using response surface method (Box-Behnken design) where the concentration of peptone and glucose in the production medium were 4 and 10 g/L, respectively. Standard error of design, ANOVA, coefficients in terms of coded factors, coded equation, fit statistics, Pareto chart, predicted versus actual values, optimizing values, and ANOVA for the quadratic model were analyzed.

TABLE 1

Factors Impacting Biomass Production

| Run Order | Peptone (g/L) | Glucose (g/L) | pH | T | RPM | R(biomass) (g/50 mL) |
|---|---|---|---|---|---|---|
| 1 | 2 | 20 | 5.6 | 20 | 100 | 0.16 |
| 2 | 2 | 10 | 7.6 | 20 | 0 | 0.18 |
| 3 | 2 | 20 | 5.6 | 30 | 0 | 0.13 |
| 4 | 4 | 20 | 7.6 | 30 | 100 | 0.35 |
| 5 | 2 | 10 | 5.6 | 30 | 100 | 0.33 |
| 6 | 4 | 10 | 7.6 | 20 | 100 | 0.31 |
| 7 | 2 | 10 | 7.6 | 30 | 100 | 0.3 |
| 8 | 4 | 10 | 5.6 | 20 | 0 | 0.15 |
| 9 | 2 | 20 | 7.6 | 20 | 0 | 0.15 |
| 10 | 4 | 20 | 7.6 | 30 | 0 | 0.14 |
| 11 | 4 | 10 | 5.6 | 30 | 0 | 0.13 |
| 12 | 4 | 20 | 5.6 | 20 | 100 | 0.25 |

TABLE 2

Optimizing Biomass Production

| | RPM | pH | T | R |
|---|---|---|---|---|
| 1 | 0 | 1 | −1 | 0.15 |
| 2 | −1 | 0 | −1 | 0.18 |
| 3 | 1 | 0 | −1 | 0.27 |
| 4 | −1 | 1 | 0 | 0.19 |
| 5 | 1 | 1 | 0 | 0.22 |
| 6 | 1 | −1 | 0 | 0.39 |
| 7 | 1 | 0 | 1 | 0.43 |
| 8 | 0 | −1 | −1 | 0.26 |
| 9 | 0 | 1 | 1 | 0.28 |
| 10 | −1 | −1 | 0 | 0.27 |
| 11 | −1 | 0 | 1 | 0.25 |
| 12 | 0 | 0 | 0 | 0.25 |
| 13 | 0 | −1 | 1 | 0.37 |

According to the production optimization analysis described above, culture production included the following steps: preparing a broth including 4 gm/L peptone and 10 mg/L glucose (5.5±1 pH), sterilizing 3000 mL of the broth (4 gm/L peptone, 10 mg/L glucose, 5.5±1 pH) using autoclave at 121° C. for 10 minutes, leaving the broth at room temperature for one hour, then inoculating 10 mL of the spore's suspension. Fermentation was conducted at 28±1° C. for 14 days using a shaking incubator at 199 rpm. The mycelia were collected from broth using centrifugation at 1000×g for 10 minutes, then the mycelia were washed using sterile 0.89% (w/v) sodium chloride solution three times at 25° C. The mycelia were collected and used for production of the 1,3-diolinoleate.

Example 4

Extraction 24 g of the lyophilized mycelial biomass were placed in conical flask and extracted with 200 ml chloroform at room temperature and allowed to stand overnight. This procedure was repeated until the mycelial material was exhausted and yielded a crude chloroform extract. Then, the crude chloroform extract was filtered and concentrated using a rotary evaporator (45 rpm and 40° C.) to get 290 mg of a dry chloroform extract. After drying, the mycelial material was extracted with 200 ml methanol and the same procedure was used to obtain 70 mg of the methanolic extract.

Example 5

Isolation of Compounds and Identification

Part of the chloroform-extract (180 mg) was separated using column chromatography on a pre-packed sephadex LH20 column (70 g, 1 cm i.d.×80 cm). The elution was performed with a mixture of chloroform:methanol (2:1), and washed with pure methanol. TLC analysis of the collected fractions with vanilin/sulfuric acid and heating at 100° C. provided 6 fractions (factions A to F).

Fraction B (65 mg) which contained three major spots was rechromatographed using Sephadex LH20 column (70 g, 1 cm i.d.×80 cm) and eluted with methanol to give Compound 1 (11 mg). Fraction D (35 mg) was re-chromatographed using chromatotron (2 mm thickness) and the elution started with a gradient ethylacetate:hexane (3% to 50%). After checking the thin-layer chromatography (TLC), homogenous fractions were pooled to afford eight subfractions (D1-D8). Subfraction D4 which was eluted with 15% ethylacetate:hexane gave Compound 2 (3 mg). Subfraction D6 which was eluted with 20% ethylacetate:hexane gave Compound 3 (4 mg).

A major compound in subfraction C (9 mg) was cleaned on preparative TLC plate (2 mm) and eluted with 30% ethyacetate:hexane to give compound 4 (1.6 mg). For the examples that follow, only compound 1 was characterized and used for future investigations.

Example 6

Elucidation of the Chemical Structure

The $^1$H, $^{13}$C and 2D-NMR spectra were recorded on a Bruker AMX-500 spectrometer. The chemical shift values are expressed in (ppm) units using tetramethylsilane (TMS) as internal standard and the coupling constants (J) are expressed in hertz (Hz). Spectroscopic grade of $CDCl_3$ was used as a solvent.

Example 7

Gas Chromatography-Mass Spectroscopy (GC-MS) Analysis

The GC-MS examinations were directed on a gas chromatograph (Hewlett-Packard 5890 series II) connected to a mass spectrometer (VG Analytical 70-250S). Fused silica packed in capillary Elite-5MS column (30 m×0.25 mm i.d., film thickness 0.25 m, from Perkin Elmer, USA) was used as a stationary phase. The mobile phase utilized was helium at a stream rate of 1 ml/min. A temperature of the injector was set at 200° C. The analysis began with heating up the oven at 60° C. and then steadily increasing it to 300° C. The final step of the process was to keep the oven at 300° C. for a 20-minute period. An election impact ionization system with an ionization energy of 70 eV was utilized for GC-MS detection. A scan rate of 0.6 seconds was utilized to cover the mass range of 35 to 600 m/z.

Example 8

Anti-Fungal Test

The biological activity of compound 1 (linoleic acid) as an antifungal agent against fluconazole- and caspofungin-resistant C. auris was evaluated using disk diffusion assay for determining the inhibition zone (mm) and two-fold serial microdilution assay for determining the minimal inhibitory concentration (MIC) (mg/mL) according to Dilika et al., (2000) and Zheng et al., (2005). The hexadecanoic acid and isopropyl myristate were prepared (both compounds (data not shown) were used in this stage as a negative control). The fluconazole and caspofungin were tested and the results showed that C. auris strain was resistant to both standard anti-fungal drugs.

The macroscopic and microscopic features of T. claveryi showed that the fruiting bodies (Ascocarps) were reddish to brown and of varying sizes. The ascus was spherical to oval with double-walls and included eight ascospores. The ascospores had thick walls and the fungal hyphae in a section of an ascospore appeared transparent. The ascospores suspension was prepared in sterile normal saline solutions, and the viability of ascospores was $10^6$ per mL.

It was demonstrated that glucose, peptone, pH, RPM, and temperature have a direct effect on standard error of design. The ANOVA analysis of selected factorial model reported a significant effect ($p<0.05$) (Table 3). The Coded equation of biomass (g/50 mL) was R=+0.2150+0.0067*A−0.0183*B−

0.0233*C+0.0150*D+0.0683*E, where A=peptone (g/L), B=glucose (g/L), C=pH, D=temperature, and E=RPM.

The Pareto chart (FIG. 1) showed that RPM, temperature, and peptone (g/L) have positive effects on biomass production while the increase in glucose (g/L) and pH have negative effects. Optimization analysis for the most important factors showed that there are significant effects (Table 4) of three values selected for RPM, pH and temperature. The Coded equation of biomass (g/50 mL) was:

$$R = +0.2500 + 0.0525*A - 0.0563*B + 0.0588*C - 0.0225*AB + 0.0225*AC + 0.005*BC + 0.0175*A^2 + B^2 + 0.015*C^2 \text{ (where } A = \text{RPM}, B = \text{pH and } C = \text{Temperature)}.$$

TABLE 3

ANOVA for selected factorial model

| Source | Sum of Squares | df | Mean Square | F-value | p-value |
|---|---|---|---|---|---|
| Model | 0.0698 | 5 | 0.0140 | 7.06 | 0.0169 significant |
| A-Peptone (g/L) | 0.0005 | 1 | 0.0005 | 0.2697 | 0.6221 |
| B-Glucose (g/L) | 0.0040 | 1 | 0.0040 | 2.04 | 0.2032 |
| C-pH | 0.0065 | 1 | 0.0065 | 3.30 | 0.1190 |
| D-T | 0.0027 | 1 | 0.0027 | 1.37 | 0.2870 |
| E-RPM | 0.0560 | 1 | 0.0560 | 28.33 | 0.0018 |
| Residual | 0.0119 | 6 | 0.0020 | | |
| Cor Total | 0.0817 | 11 | | | |

Response = Biomass production (g/50 ml)

TABLE 4

ANOVA for Quadratic model
Response 1: Biomass production

| Source | Sum of Squares | df | Mean Square | F-value | p-value |
|---|---|---|---|---|---|
| Model | 0.0803 | 9 | 0.0089 | 12.59 | 0.0304 significant |
| A-RPM | 0.0220 | 1 | 0.0220 | 31.13 | 0.0114 |
| B-PH | 0.0253 | 1 | 0.0253 | 35.74 | 0.0094 |
| C-T | 0.0276 | 1 | 0.0276 | 38.98 | 0.0083 |
| AB | 0.0020 | 1 | 0.0020 | 2.86 | 0.1895 |
| AC | 0.0020 | 1 | 0.0020 | 2.86 | 0.1895 |
| BC | 0.0001 | 1 | 0.0001 | 0.1412 | 0.7321 |
| $A^2$ | 0.0007 | 1 | 0.0007 | 0.9882 | 0.3934 |
| $B^2$ | 0.0000 | 1 | 0.0000 | 0.0000 | 1.0000 |
| $C^2$ | 0.0005 | 1 | 0.0005 | 0.7261 | 0.4568 |
| Residual | 0.0021 | 3 | 0.0007 | | |
| Cor Total | 0.0824 | 12 | | | |

Coded equation: Biomass (g/50 mL) = +0.2500 + 0.0525 * A − 0.0563 * B + 0.0588 * C − 0.0225 * AB + 0.0225 * AC + 0.005 * BC + 0.0175 * $A^2$ + $B^2$ + 0.015 * $C^2$ Where A = RPM, B = pH and C = Temperature The influence of RPM, pH, and temperature on standard error of design using 3D surface model reported that standard error of RPM and pH decreased when a high value of peptone (g/L) was used. There was an increase in predication of biomass production when a high value of RPM, a high value of temperature, and a low pH value were used. The results confirmed that the best-predicated biomass production could be obtained when this equation (+0.996*RPM−0.981*pH+0.947*Temperature) was applied. The yield of wet biomass reached 14 mg/mL.

Example 9

Characterization of Compound I

Compound 1 was obtained as a yellowish to colorless oily substance that readily dissolved in chloroform. The infrared spectrum (IR) revealed strong bands at 1750 and 1165 cm$^1$, showing the existence of an ester function (ester, C=O, C—O), as well as strong bands at 2910 and 2845 cm$^1$, suggesting the presence of methylene groups. Numerous NMR data were acquired for the purpose of elucidating the structure of this chemical, including $^1$H, $^{13}$C, DEPT-135, HSQC, 1H-1H COSY, and HMBC. The $^{13}$C-NMR spectrum revealed the presence of 39 carbon signals, including signals at 173.00 and 173.46 corresponding to two ester carbonyl C-atoms, four olefinic methine carbons at 128.02 and 130.13. A signal at 69.00 corresponded to methine carbon, and one signal at 62.23 corresponded to methylene carbon, indicating the presence of a diglyceride (ester of glycerol with two linoleic acids). The 1H-NMR spectrum of compound 1 revealed distinctive signals at 0.87 and 0.89 as two triplets of three protons indicative of two terminal $CH_3$-groups, at 1.29 as a broad singlet indicative of a long chain of $CH_2$-protons, at 2.19 and 2.375 indicative of $CH_2$-groups to carbonyl groups. In addition, a multiplet signal of four protons at δ 5.33 was attributed to olefinic protons. Compound 1 was identified as a glyceryl 1,3-dilinoleate (1,3-dilinoleoyl glycerol). It is also called 1,3-Diolein, based on NMR data and comparison to published data.

Example 10

Anti-fungal Activity of Linoleic Acid produced from Mycelia of *T. claveryi*

Linoleic acid produced as described in the Examples above demonstrated biological activity as antifungal agent. The inhibition zone of 0.1 mg/disk was 12 mm and the MIC of this fatty acid was 0.048 mg/mL fluconazole- and caspofungin-resistant *C. auris*.

It is to be understood that the method for producing 1,3-diolein from biomass is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for producing 1,3-diolein comprising:
   a) extracting a mycelial biomass obtained from truffles; and
   b) isolating the 1,3-diolein f rom the extract.

2. The method of claim 1, wherein the extract is a chloroform extract.

3. The method of claim 1, wherein isolating the 1,3-diolein comprises using column chromatography.

4. The method of claim 1, wherein the truffles are desert truffles.

5. The method of claim 4, wherein the desert truffles are of the species *T. claveryi*.

6. The method of claim 1, wherein the mycelial biomass is a truffle-derived biomass cultivated using ascospores of *T. claveryi*.

7. The method of claim 6, wherein the truffle-derived biomass is prepared by:
   mixing a truffle portion with a saline solution to provide a first mixture;
   centrifuging the first mixture to provide a supernatant including the ascospores;
   adding the supernatant to a broth including peptone and glucose to provide a second mixture; and
   incubating the second mixture to provide a broth including mycelia; and
   collecting the mycelia.

8. A method of inhibiting fungal growth comprising administering a therapeutically effective amount of 1,3-diolein.

9. The method of claim 8, wherein the fungus is *Candida auris*.

10. The method of claim 9, wherein the *Candida auris* comprises antifungal-drug-resistant *C. auris* strains.

* * * * *